United States Patent [19]

Sawada et al.

[11] Patent Number: 5,270,196
[45] Date of Patent: Dec. 14, 1993

[54] ARYLSULFATASE FROM *STREPTOMYCES*

[75] Inventors: Yosuke Sawada, Tokyo; Tomokazu Ueki; Satoshi Yamamoto, both of Kanagawa; Koji Tomita, Tokyo; Yasuo Fukagawa; Toshikazu Oki, both of Kanagawa, all of Japan

[73] Assignee: Bristol-Myers Squibb Company, New York, N.Y.

[21] Appl. No.: 827,252

[22] Filed: Jan. 29, 1992

Related U.S. Application Data

[63] Continuation of Ser. No. 424,376, Oct. 20, 1989, abandoned.

[51] Int. Cl.$^5$ .............................................. C12N 9/16
[52] U.S. Cl. ..................................... 435/196; 435/886
[58] Field of Search ..................... 435/196, 886–906

[56] References Cited

FOREIGN PATENT DOCUMENTS 302473  2/1989  European Pat. Off. .
192793  8/1988  Japan .

OTHER PUBLICATIONS

Sigma Catalog, pp. 1304–1305 (1988).
Murooka, Y, Appl. Environ Micro Biol 39(4):812–17 (1980).
Murooka, Y, BBA 485:134–40 (1977).
Bateman, T., Biochem J. 236:401–408 (1986).
Okamura H., Agr Biol Chem 40:2071–76 (1976).
Balasubramanian K., J. Neuro Chem 27:485–92 (1976).
Farooqui A., Biochem J., 242:97–102 (1987).
Tsukamura M. Micro Biol Immol. 26:1101–19 (1982).
A. B. Roy, "The Enzymes," vol. 5, pp. 1–19, P. D. Boyer, Ed., Academic Press, 1971, *The Hydrolysis of Sulfate Esters*.
A. B. Roy, "The Enzymes," vol. 5, pp. 21–41, P. D. Boyer, Ed., Academic Press, 1971, *Arylsulfatases*.
G. D. Lee, et al., "Arch. Biochem. Biophys.," 166, pp. 280–294, 1975, *Purification and Properties of a Homogeneous Aryl Sulfatase A from Rabbit Liver*.
L. W. Nichol, et al., "J. Biochem.," 55, pp. 643–651, 1964, *The Sulphatase of Ox Liver*.
E. R. B. Graham, et al., "Biochim. Biophys. Acta," 329, pp. 88–92, 1973, *The Sulphatase of Ox Liver*.
Y. L. Steintiz, "Eur. J. Appl. Microb. Biotechnol.," 13, pp. 216–221, 1981, *Microbial Desulfonation of Lignosulfonate–A New Approach*.
P. F. Stanbury and A. Whitaker, "Principles of Fermentation Technology," Pergamon Press, 1984, pp. 78–80, 188, and 196.

*Primary Examiner*—Douglas W. Robinson
*Assistant Examiner*—S. Saucier
*Attorney, Agent, or Firm*—Mollie M. Yang

[57] ABSTRACT

The present invention relates to an arylsulfatase of microbial origin. The enzyme may be linked to an antibody against a tumor-associated antigen and the resulting conjugate used in conjuction with a sulfated prodrug of a 4'-demethylepipodophyllotoxin glucoside derivative, particularly etoposide in cancer chemotherapy.

3 Claims, 3 Drawing Sheets

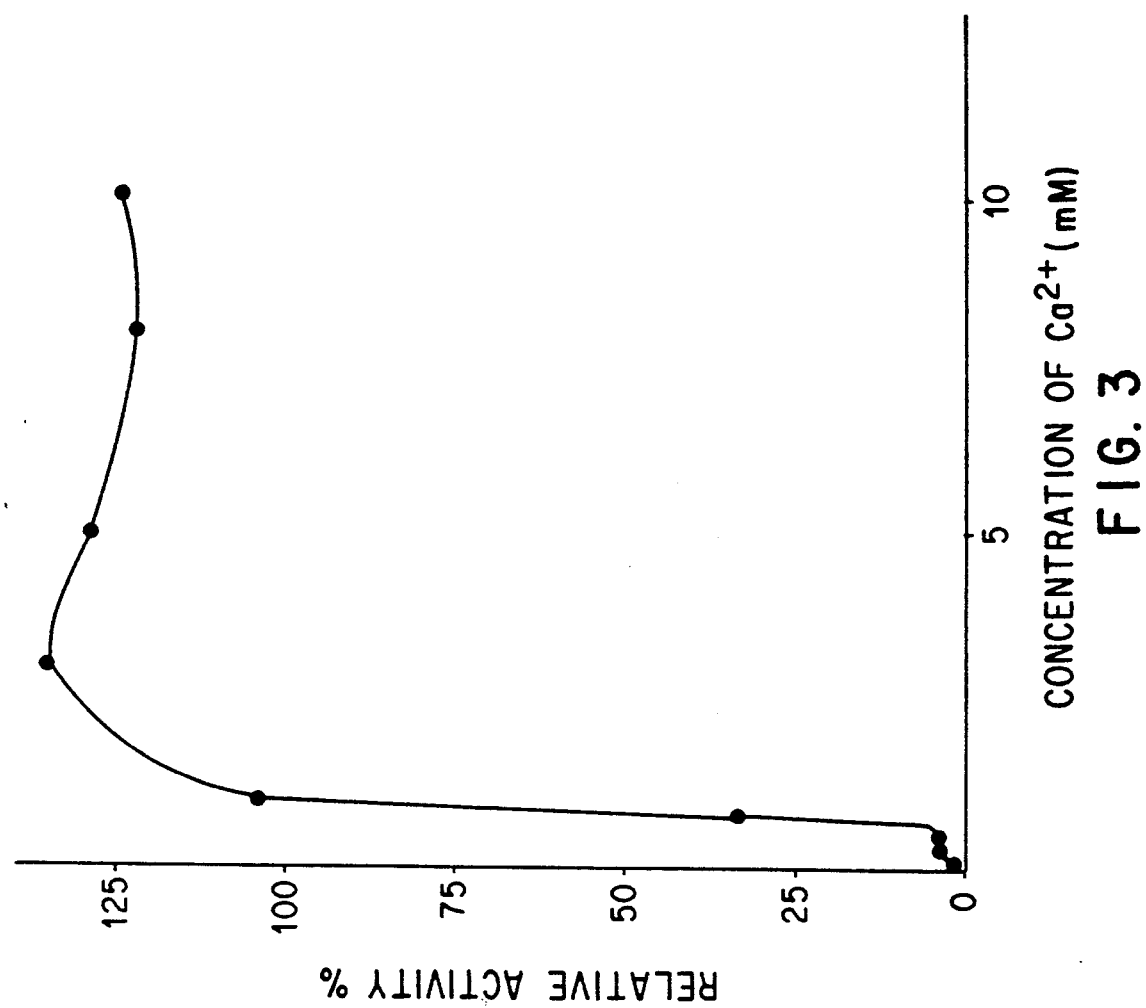

ARYLSULFATASE FROM *STREPTOMYCES*

CROSS REFERENCE TO RELATED APPLICATION

This application is a continuation of our co-pending application Ser. No. 07/424,376 filed Oct. 20, 1989, now abandoned.

BACKGROUND OF THE INVENTION

The present invention relates to a sulfatase and a method for its production by fermentation. More particularly, it relates to a sulfatase isolated from a species of Streptomyces.

One of the major problems in human cancer chemotherapy is the nonspecific action of antitumor agents which can cause unwanted damage to normal cells. Numerous attempts have been made to more selectively deliver a cytotoxic agent to or near the tumor site thereby minimizing toxicity to normal tissues. A great deal of effort in this area has been devoted to linking a cytotoxic agent to a second component which may have a higher affinity for tumor cells than for normal cells, for example an antibody, a hormone, a lectin, or a polymer.

More recently, a different approach has been proposed which involves administering to a tumor bearing host a prodrug of an antitumor agent in conjunction with an antibody-enzyme (ab-enz) conjugate [see, e.g., P. D. Senter, et al., European Application 302,473, published Feb. 8, 1989]. The conjugate consists of an enzyme that is capable of converting the prodrug into the active parent compound and a tumor-specific antibody which serves to bring the enzyme to the tumor cell surface where the enzyme would act on the prodrug. This method can, thus, potentially create a higher concentration of the antitumor drug in the vicinity of the tumor to which the ab-enz conjugate is bound. For use in the ab-enz conjugate/prodrug approach, the enzyme is preferably one that is not present in the blood stream in very high concentration in order that the prodrug may remain intact until it encounters the enzyme at the tumor site. The prodrug itself may be considerably less cytotoxic than the parent drug; the cytotoxic drug may be one of the commonly used antitumor agents that is amenable to modification to produce a prodrug which can regenerate the parent drug enzymatically.

Etoposide (Ia) and teniposide (Ib) are two clinically established antitumor drugs belonging to a class of compounds generally known as 4'-demethylepipodophyllotoxin glucosides (DEPG). The general structure of 4'-demethylepipodophyllotoxin glucosides is depicted below as formula (I) wherein $R^1$ may be, for example, $C_{1-10}$alkyl, 2-thienyl, furyl, or phenyl:

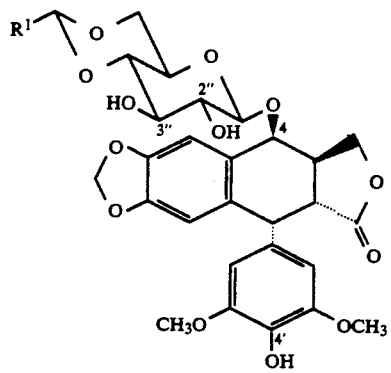

Ia: $R^1 = CH_3$
Ib: $R^1 = $ 2-thienyl

The hydroxyl groups and phenol group of DEPG may be derivatized to provide a suitable prodrug as substrate for an ab-enz conjugate. In fact, the effectiveness of etoposide 4'-phosphate in combination with a monoclonal antibody-alkaline phosphatase conjugate has been demonstrated in a murine human colon carcinoma xenograft model [Senter, et al., supra].

In addition to etoposide 4'-phosphate, etoposide sulfates are also compounds known in the art. These derivatives are disclosed in Japanese Kokai 88/192,793 and are depicted as formula (II) below:

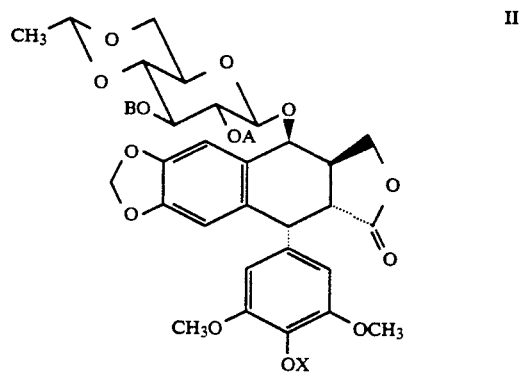

wherein one of A, B, and X is the group $-SO_3H$ and the others are H.

Etoposide 4'-sulfate (A=B=H; X=$-SO_3H$) appears to be much less cytotoxic than etoposide itself, requiring a very large dose to achieve the same degree of activity as etoposide. This may indicate that etoposide 4'-sulfate is not facilely converted into etoposide in vivo and, thus, may be more suitably used as a prodrug in combination with an ab-enz conjugate. The enzyme needed to effect the conversion of etoposide 4'-sulfate into etoposide would be a sulfatase which catalyzes the hydrolysis of a sulfate ester to the corresponding hydroxyl compound as follows:

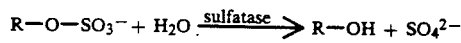

Several types of sulfatase have so far been studied, and these include Type I and Type II arylsulfatases, steroid sulfatases, glycosulfatases, choline sulfatases, alkylsulfatases, and myrosulfatases. (For a review on sulfatases, see "The Hydrolysis of Sulfate Esters" by A. B. Roy in "The Enzymes", vol. V, pp. 1–19, P. D. Boyer, Ed., Academic Press, 1971.) Among these, arylsulfatases (aryl sulfate sulfohydrolase, EC 3.1.6.1), which catalyzes the above reaction where R is an aromatic ring, have been isolated from various animal tissues, as well as microbial sources, and have been most extensively studied (for a review on arylsulfatases, see "Arylsulfatases" by R. G. Nicholls and A. B. Roy, ibid, pp. 21–41). It is noteworthy that, even though many sulfatases have been reported, few have been purified to homogeneity. For example, arylsulfatase A from rabbit liver has a molecular weight of approximately 70 kD (monomer), forms a dimer at pH 7.4 and tetramer at pH 4.8, and has been purified 10,000 fold (G. D. Lee and R. L. Van Etten; Arch. Biochem. Biophys., 166, 280–294, 1975); arylsulfatase isolated from ox liver is a glycoprotein having a molecular weight of 107 kD (monomer) (L. W. Nichol and A. B. Roy; J. Biochem., 55, 643–651, 1964 and E. R. B. Graham and A. B. Roy; Biochim. Biophys. Acta, 329, 88–92, 1973).

Arylsulfatase activity in releasing sulfate from lignosulfonate was demonstrated in cell free extracts of Streptomyces sp. L.; however, the enzyme itself was not purified or characterized (Y. L. Steinitz, Eur. J. Appl. Microb. Biotechnol., 13, 216–221, 1981).

Arylsulfatases isolated from various sources are available commercially. These enzymes have been evaluated using etoposide 4'-sulfate as the substrate; however, most of these showed either no or little hydrolytic activity against this compound. Furthermore, none of the commercially available sulfatases are homogeneous and some have unfavorable characteristics such as high molecular weight, low optimum pH, etc., rendering them unsuitable for clinical use.

Against this background, a program was initiated to screen for microbial arylsulfatases which are capable of hydrolyzing a 4'-demethylepipodophyllotoxin glucoside 4'-sulfate to the corresponding 4'-demethylepipodophyllotoxin glucoside. The result of this effort forms the basis of the present invention.

SUMMARY OF THE INVENTION

Figure 1B:
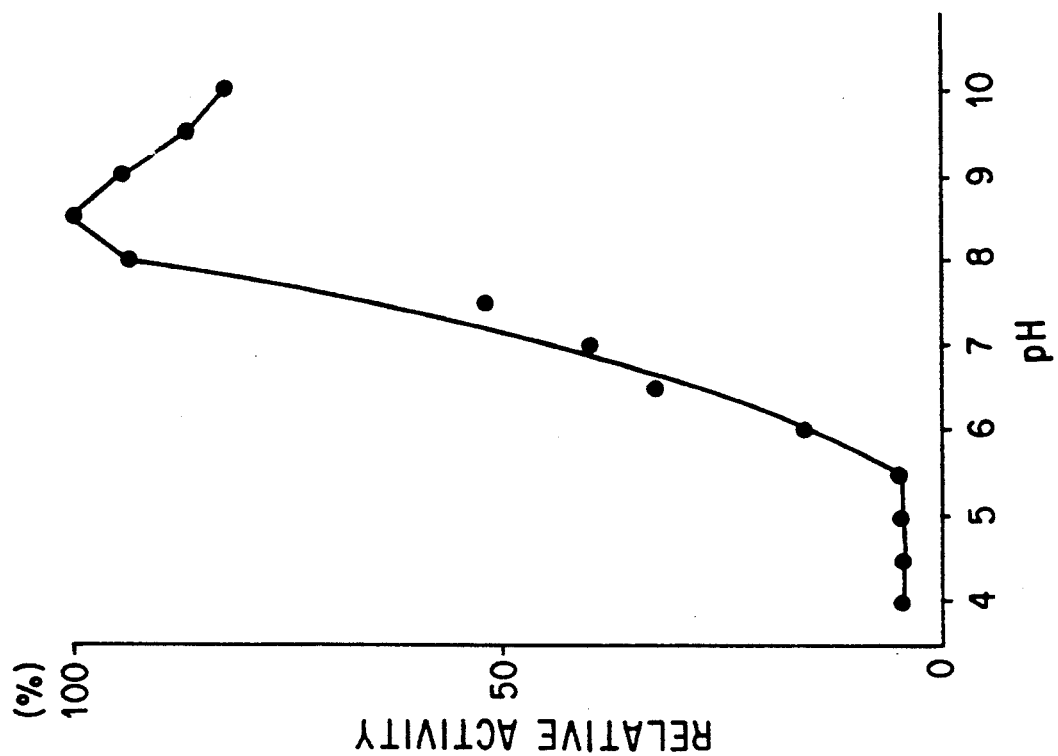
FIGS. 1A and 1B show the activity and stability profiles, respectively, of Es-2 sulfatase as a function of pH.

The present invention provides a sulfatase capable of catalyzing the conversion of a 4'-demethylepipodophyllotoxin glucoside 4'-sulfate into the corresponding 4'-demethylepipodophyllotoxin glucoside.

A further aspect of the present invention provides a method of producing the sulfatase which comprises aerobically cultivating an enzyme producing Streptomyces sp. in a medium containing an assimilable source of carbon and nitrogen until a recoverable amount of the enzyme has been formed, and recovering said sulfatase.

Yet another aspect of the present invention provides a sulfatase producing microorganism Streptomyces sp. T109-3, or a mutant thereof, or a variant thereof.

DETAILED DESCRIPTION OF THE INVENTION

The present invention provides a sulfatase designated herein as Es-2 isolated from an actinomycetes, specifically Streptomyces sp. T-109-3; said sulfatase has a molecular weight of about 45 kD, as determined by SDS-PAGE, and an isoelectric point of about 5.6. The enzyme is capable of catalyzing the conversion of a 4'-demethylepipodophyllotoxin glucoside 4'-sulfate into a 4'-demethylepipodophyllotoxin glucoside as depicted below:

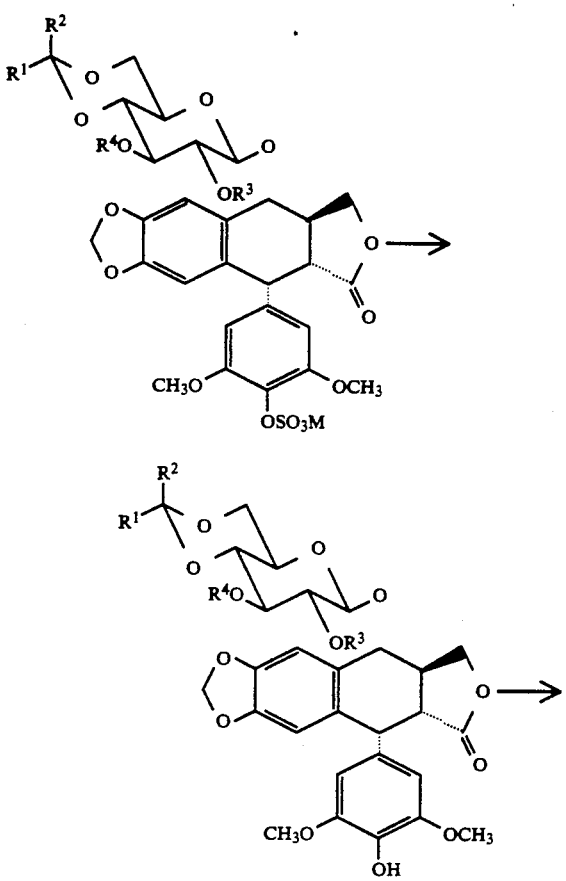

wherein $R^1$ and $R^2$ are each $(C_{1-10})$alkyl, or $R^2$ is H and $R^1$ is selected from the group consisting of $C_{1-10}$alkyl, furyl, thienyl, and phenyl; $R^3$ and $R^4$ are each independently H or an acyl group; and M is H or an alkali metal ion. Acyl group may include, but is not limited to, formyl, acetyl, and benzoyl. Alkali metal ion is, for example, lithium, sodium, and potassium. More particularly, the substrate for Es-2 is etoposide 4'-sulfate or an acylated derivative thereof.

As used herein, "substantially purified" enzyme represents the enzyme showing a single band upon SDS-polyacrylamide gel electrophoresis.

I. PRODUCING ORGANISM

An actinomycete strain No. T109-3 was isolated from a soil sample collected in Maharashtra State, India. A biologically pure culture of the microorganism designated as Streptomyces sp. strain T109-3 has been deposited with the American Type Culture Collection, Rockville, Md., under the accession number ATCC 53948.

(a) Morphology

Strain T109-3 forms abundant aerial mycelium on the branched and non-fragmentary substrate mycelium. Long and closed-spiral spore-chains are born monopodially on the tip of aerial hyphae. The spore-chains contain 10 to 50 spores per chain. The spores are oblong (0.6–0.8×1.0–1.2 μm), non-motile, and have a spiny surface. Sclerotia or sporangia-like bodies are not formed.

(b) Cultural Characteristics

Strain T109-3 grows well on all ISP media and Czapek's sucrose-nitrate agar. The aerial mycelium turns olive gray or brownish gray after sporulation. The substrate mycelium is colorless or light yellow. Melanin and other distinct pigments are not produced. The culutral characteristics of strain T109-3 are listed in Table I.

TABLE I
Cultural Characteristics of Strain T109-3

| Medium | Growth | Aerial Mycelium | Substrate Mycelium | Diffusible Pigment |
| --- | --- | --- | --- | --- |
| Sucrose-nitrate agar (Czapek-Dox agar) | Good | Good; yellowish white (92) and medium gray | Light yellow (86) | None |
| Tryptone-yeast extract broth (ISP No. 1) | Moderate, not turbid | None | Colorless | None |
| Yeast extract-malt extract agar (ISP No. 2) | Good | Good; light olive gray (112) | Light yellowish brown (76) | None |
| Oatmeal agar (ISP No. 3) | Moderate | Good; light brownish gray (63) | Colorless | None |
| Inorganic salts-starch agar (ISP No. 4) | Moderate | Good; olive gray (113) | Colorless | None |
| Glycerol-asparagine agar (ISP No. 5) | Moderate | Poor; white to light gray | Colorless to light yellow (86) | None |
| Peptone-yeast extract-iron agar (ISP No. 6) | Moderate | None | Pale yellow (89) | Pale yellow (89) |
| Tyrosine agar (ISP No. 7) | Moderate | Poor; white | Colorless to light yellow (86) | None |
| Glucose-asparagine agar | Poor | None | Colorless | None |
| Nutrient agar | Moderate | Scant; white | Yellowish white (92) | Light yellow (86) |

Observation after incubation at 28° C. for 3 weeks. Color name used: ISCC-NBS color-name charts.

(c) Physiological Characteristics

Strain T109-3 hydrolyzes gelatin, and nitrate reductase and tyrosinase are not formed. Profiles of sugar utilization are as follows: positive for sucrose, raffinose, D-melezitose, inositol, and D-mannitol; negative for L-arabinose and L-rhamnose. Physiological characteristics of strain T109-3 are listed in Table II.

TABLE II
Physiological Characteristics of Strain T109-3

| Hydrolysis of: | | Utilization of:* | |
| --- | --- | --- | --- |
| Gelatin | + | Glycerol | + |
| Starch | + | D-Arabinose | − |
|  |  | L-Arabinose | − |
| Milk coagulation | − | D-Xylose | +(w) |
| Milk peptonization | + | D-Ribose | + |
|  |  | L-Rhamnose | − |
| Production of: |  | D-Glucose | + |
|  |  | D-Galactose | + |
| Nitrate reductase | − | D-Fructose | + |
| Tyrosinase | − | D-Mannose | + |
|  |  | L-Sorbose | − |
| Tolerance to: |  | Sucrose | + |
|  |  | Lactose | + |
| Lysozyme, 0.01% | − | Cellobiose | + |
| NaCl, 1%–9% | + | Melibiose | + |
| 10% or More | − | Trehalose | + |
| pH, 5.0–10.7 | + | Raffinose | + |
| Temperature: |  | D-Melezitose | + |
|  |  | Soluble Starch | + |
|  |  | Cellulose | − |
| Growth range | 14° C.–41° C. | Dulcitol | − |
| Optimal growth | 32° C.–38° C. | Inositol | + |
| No growth | 11.5° C. and 43° C. | D-Mannitol | + |
|  |  | D-Sorbitol | − |
|  |  | Salicin | +(w) |

*Basal medium: Pridham-Gottlieb' inorganic medium (ISP No. 9).
+(w): Weakly positive

(d) Cell Chemistry

Whole cell hydrolysate contains LL-diaminopimelic acid. Phospholipids contain two phosphatidylethanolamines (PE), phosphatidylglycerol (PG), and phosphatidylinositol (PI). Therefore, the strain belongs to cell wall Type I and phospholipid Type P-II.

Based on the spore-chain morphology and cell chemistry of strain T109-3, the strain was placed in the genus Streptomyces. According to the classification keys of Streptomyces by Pridham and Tresner [Pridham, T. G., and H. D. Tresner: Genus Streptomyces Waksman and Henrici, pp. 748–829 in R. E. Buchanan and N. E. Gibbons (Ed.) Bergey's Manual of Determinative Bacteriology, 8th Ed., 1974, Williams & Wilkins Co., publ.], the strain is assigned to the gray (GY), Spira (S), non-chromogenic (C-), and spiny (SPY) group. Among 24 known species of the above group of species described by Pridham and Tresner, strain T190-3 is similar to S. albospinus M750-G1, S. albulus ATCC 12757, S. chattanoogensis ATCC 13358, and S. noursei ATCC 11455 in its sugar utilization profile. Further comparisons of strain T109-3 to the above four species indicated that strain T109-3 is similar to S. noursei. However, strain T109-3 differs from S. noursei in several characteristics as shown in Table III. Thus, strain T109-3 has been designated as a new strain of Streptomyces sp.

TABLE III

Differential Characteristics of Strain T109-3 from *Streptomyces noursei* NRRL 1714

|  | Strain T109-3 | S. noursei NRRL 1714 |
|---|---|---|
| Cultural characteristics: | | |
| Growth on Czapek's sucrose-nitrate agar | Good (abundant formation of aerial mycelium) | Very scant (colorless thin substrate mycelium) |
| Reverse color in: | | |
| ISP medium Nos. 3, 4, and 5 | Colorless, yellow or yellowish gray | Dark grayish yellow or olive brown |
| ISP medium No. 7 | Grayish yellow | Dark purplish gray |
| Utilization of sugars: | | |
| Lactose | + | − |
| Cellobiose | +(w) | − |
| Melibiose | + | − |
| Raffinose | + | − |
| D-Melezitose | + | − |

II. ENZYME PRODUCTION

The arylsulfatase Es-2 of the present invention is produced by cultivating Streptomyces sp. strain T109-3 or a mutant thereof under submerged conditions in an aqueous nutrient medium. The producing organism is grown in a nutrient medium containing an assimilable carbon source, for example an assimilable carbohydrate. Example of suitable carbon sources include cerelose, fructose, soluble starch, and glycerol. The nutrient medium should also contain an assimilable nitrogen source such as fish meal, yeast extract, or ammonium salts. Inorganic salts such as sodium chloride, potassium chloride, magnesium sulfate, calcium carbonate, phosphates, etc., and trace elements such as copper, manganese, iron, zinc, etc., are added to the medium if necessary, or they may be present as impurities of other constituents of the medium. The incubation temperature may be any temperature at which the producing strain is able to grow and produce the desired product, e.g., from about 18° C. to about 39° C., but it is preferable to conduct the fermentation at about 25° C.-35° C., most preferably at about 25° C.-30° C. A neutral pH is preferably employed in the medium, and production of the enzyme is generally carried out for a period of about 4 to 8 days. Ordinarily, optimum production is achieved in about 5-6 days. For preparation of relatively small amounts of the enzyme, shake flask or surface culture can be employed, but for the preparation of larger amounts, submerged aerobic culture in sterile tanks is preferred. When tank fermentation is to be carried out, it is desirable to produce a vegetative inoculum in a nutrient broth by inoculating the broth with spores from the organism and, when a young active vegetative inoculum has been obtained, transferring the inoculum aseptically to the fermentation tank medium. Further agitation may be provided with a mechanical impeller. Antifoam agents, such as lard oil or silicone oil, may also be added if needed.

It is to be understood that the present invention is not limited to the use of the particular preferred Streptomyces sp. strain T109-3 described above or to organisms fully answering the above description. It is especially intended to include other strains or mutants of the said organism which can be produced by conventional means, such as x-rays radiation, ultraviolet radiation, treatment with nitrogen mustards, phage exposure, and the like, and which retain the ability to produce the arylsulfatase Es-2 of the present invention.

III. ISOLATION AND PURIFICATION OF ENZYME

The arylsulfatase of the present invention may be isolated from the fermentation broth using conventional protein separation methodologies such as dialysis, ultrafiltration, gel filtration, isoelectric precipitation, salting out, electrophoresis, ion-exchange chromatography, and affinity chromatography. A combination of these techniques in sequence is generally used to purify the protein to apparent homogeneity. Protein purification is preferably carried out at reduced temperature, preferably at about 0°-5° C. The isolation and purification process may be monitored and guided by enzyme activity assay using p-nitrophenylsulfate or other suitable arylsulfates as substrate or by physical methods such as UV or HPLC techniques. A typical isolation purification sequence is provided below for illustrative purpose only, and it will be appreciated by those skilled in the art that different sequences using other methods may also be used so long as the protein is obtained in high purity and retains its biological activities.

The fermentation broth of Streptomyces sp. T109-3 is filtered to remove the insoluble mass, and the volume of the filtrate is reduced at room temperature using ultrafiltration. The concentrated solution is treated with ammonium sulfate to precipitate the protein. Ammonium sulfate is added to achieve a 70%-90% saturation, preferably 80% saturation. The solution is allowed to stand for a few hours at about 4° C., and the precipitate is collected by centrifugation at about 4° C. The pellet is dissolved in a suitable buffer, e.g. Tris-HCl at pH of about 7.5, and then dialyzed against the same buffer containing 1 mM $CaCl_2$. The precipitate is removed by centrifugation, and the supernatant is subject to purification by cation-exchange column chromatography using an adsorbant such as sulfated cellulose. The column is eluted with a suitable buffer such as 1M Tris-HCl at pH 7.5. Fractions containing sulfatase activity are combined and further purified by anion-exchange chromatogragphy using a suitable anion-exchanger such as DEAE-Cellulose. The elution buffer is suitably Tris-HCl at about pH 7.5 used in linear concentration gradient from 50 mM to 500 mM. The combined active fractions are again chromatographed on a sulfated cellulose column using a linear concentration gradient of Tris-HCl buffer at pH of about 7.5 from 50 mM to 1.5M. Active fractions are pooled and concentrated by ultrafiltration to provide the sulfatase of the present invention.

Sulfatase activity during purification is monitored by determining the conversion of p-nitrophenylsulfate into p-nitrophenol using spectrophotometric means. Specifically, the following assay method is used. 50 $\mu$l of a p-nitrophenylsulfate solution (1 mg/ml in 50 mM Tris-HCl, pH7.5), 50 $\mu$l of a sample, and 100 $\mu$l of of 50 mM Tris-HCl, pH 7.5, are mixed and incubated for 30 minutes at 37° C. If the activity is weak, the incubation time is prolonged up to 18 hours. The liberated p-nitrophenol is determined spectrophotometrically at 415 nm. From standard curves of p-nitrophenol and protein concentrations, the unit or specific activity per mg of the enzyme is calculated. The protein concentration is determined by measuring the absorption at 280 nm throughout purification and, in case of homogeneous protein, by the Bradford method [Bradford, M., et al., Anal. Biochem., 1976, 72:248-254] using bovine serum albumin as the standard protein. A unit of sulfatase activity is defined as the amount of enzyme which can hydrolyze one nanomole of p-nitrophenyl sulfate to p-nitrophenol in one minute at 37° C. at pH 7.5.

IV. CHARACTERIZATION OF SULFATASE ES-2

A. Molecular Weight (MW) Determination

(a) By Gel Filtration

Purified Es-2 sulfatase was chromatographed on TSK-GEL (TOYOPEARL, HW-55F, TOSOH, Φ2.5×70 cm: Vt, developing solvent: 250 mM Tris-HCl, pH 7.5) along with standard proteins, chymotrypsinogen (MW: 25,000), egg albumin (MW: 45,000), bovine serum albumin (MW: 67,000), and blue dextran. Eluate was fractionated in 1 ml fractions. Blue dextran was eluted at fr. no. 110 (Vo), chymotrypsinogen at fr. no. 188 (Ve), egg albumin at fr. no. 173 (Ve), bovine serum albumin at fr. no. 168 (Ve), and Es-2 at fr. no. 171 (Ve). $K_{av}$ was calculated by equation (1), and the MW of Es-2 was read from plotting $K_{av}$ against MW. By this method the molecular weight of Es-2 was determined to be about 45 kD.

$$K_{av} = (Ve - Vo) \div (Vt - Vo) \quad (1)$$

(b) By SDS-PAGE

A mixture of the sulfatase (25 μg in Tris-HCl (50 mM, 40 μl, pH7.5)), 10% sodium dodecylsulfate (SDS, 10 μl), and 50% glycerin (5 μl, containing 0.05% bromophenol blue) was heated at 98° C. for one minute. The reaction mixture was applied into a well of SDS-polyacrylamide gel. Electrophoresis was carried out in a solution of Tris-HCl (0.31%, pH 8.4), glycine 1.44%, and SDS 0.1%. Running condition was 40 mA for 2 hours at 25° C. The gel was stained with Coomassie Brilliant Blue R250 and washed with 7% acetic acid. The molecular weight of the sulfatase was determined to be about 45 kD relative to marker proteins of known molecular weights.

2-Mercaptoethanol SDS-PAGE of the purified Es-2 sulfatase preparation resulted in only one protein band showing the same mobility as the 2-mercaptoethanol untreated protein preparation. This indicates that Es-2 exists as a monomer.

B. Isoelectric Point Determination

Isoelectric point was estimated by column chromatography using Chromatofocusing gel PBE94 (Pharmacia-LKB Biotechnology). The protein was applied on top of the gel column which had been previously equilibrated with 25 mM imidazole-HCl, pH 7.4, and eluted with Polybuffer 74-HCl, pH 4.0. The pH and absorption at 280 nm of each fraction were measured. The isoelectric point of the sulfatase was determined to be about 5.6 using this method.

C. Enzyme Activity Profile

(a) Optimum pH

Figure 1A:
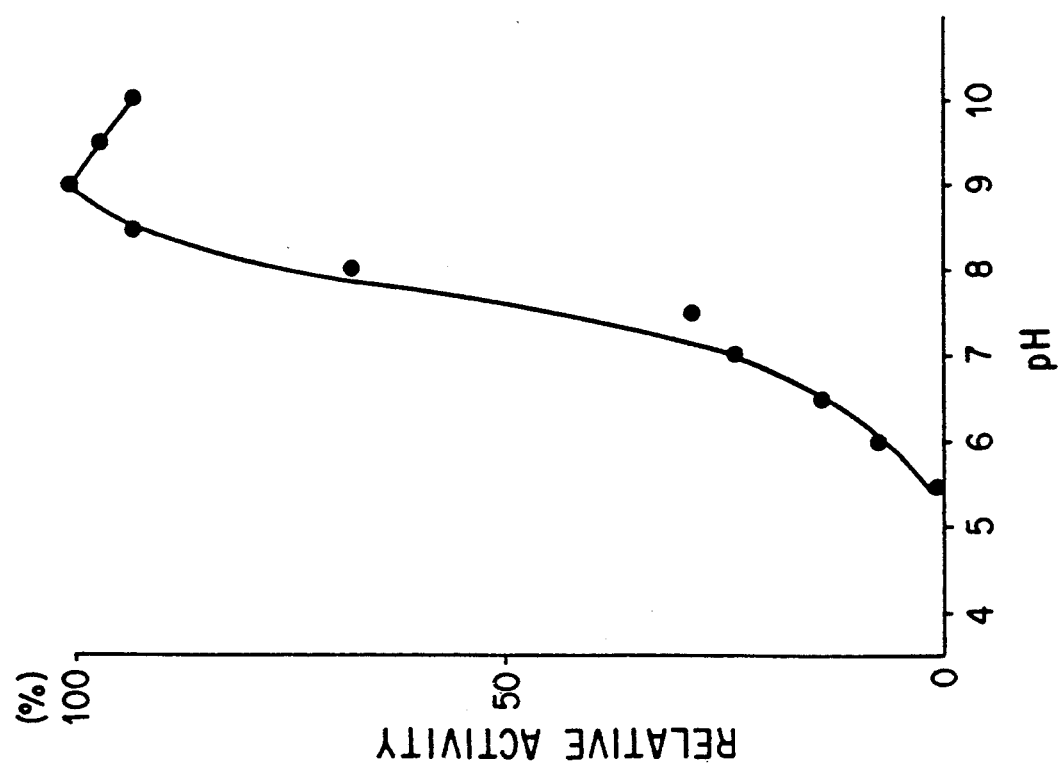

The enzyme solution (0.6 u in 50 μl of 50 mM Tris-HCl, pH 7.5) was mixed with 100 μl each of the following buffers: 500 mM sodium acetate (pH 4.0–5.5), 500 mM Tris-maleate (pH 5.5–7.7), 500 mM Tris-HCl (pH 7.5–9.0), and 500 mM glycine-NaOH (pH 9.0–10.0). The substrate, p-nitrophenylsulfate, was similarly dissolved in each of the above buffers (1 mg/ml). A sample (150 μl) from the enzyme solution is mixed with the substrate (50 μl) in the same buffer, and the mixture was incubated for 30 minutes at 37° C. The enzyme activity in each buffer was determined spectrophotometrically by UV at 415 nm. The optimal pH of the enzyme was thus determined to be about 9.0 (FIG. 1A).

b) pH Stability

The stock enzyme solution was dialyzed against water to remove salts. The enzyme solution was adjusted to 0.6 μl with Tris-HCl buffer (pH 7.5). This solution (10 μl) was mixed with 40 μl each of the buffer listed in (a) and incubated for 30 minutes at 30° C. The enzyme sample (50 μl) was mixed with 100 μl of 500 mM Tris-HCl (pH 9.0) and 50 μl of substrate in water (1 mg/ml), and the mixture was incubated at 37° C. for 30 minutes to determine the residual enzyme activity. The enzyme showed maximum stability at pH of about 8.5 (FIG. 1B).

(c) Optimum Temperature

Figure 2B:
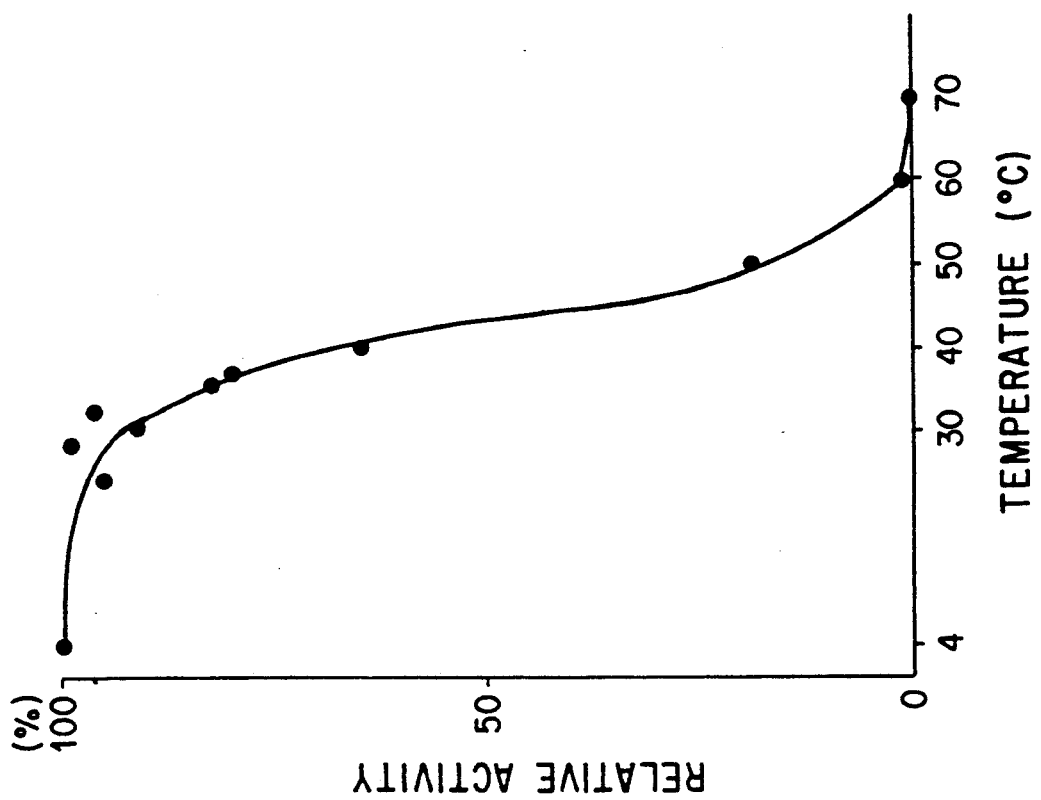
FIGS. 2A and 2B show the activity and stability profile, respectively, of Es-2 sulfatase as a function of temperature.
Figure 2A:
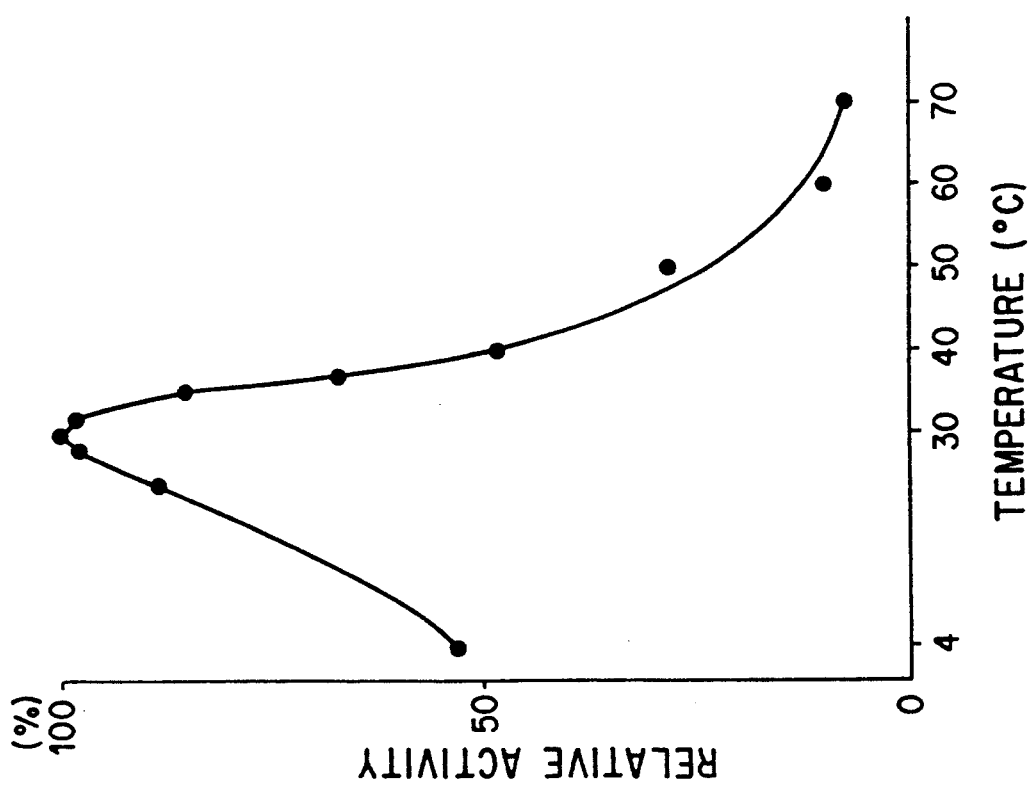

Enzyme (0.6 u) in 150 μl of 50 mM Tris-HCl (pH 9.0) were incubated with p-nitrophenylsulfate (1 mg/ml, 50 μl) in the same buffer (pH 9.0) for 30 minutes at various temperatures (200 μl each). The optimal temperature for enzyme activity was shown to be about 30° C. (FIG. 2A).

(d) Temperature Stability

Enzyme preparations (0.6 u) in 50 mM Tris-HCl (150 μl, pH 9.0) were incubated for 15 minutes at various temperatures and then cooled in an ice bath. p-Nitrophenylsulfate (1 mg/ml, 50 μl) was added to the enzyme solution, and the mixture was incubated for 30 minutes at 37° C. The enzyme was stable below 30° C. at pH 9.0 (FIG. 2B).

(e) Effect of Ions

Enzyme (0.6 u), p-nitrophenyl sulfate 4 mM, and ion 1 mM were dissolved in 200 μl of Tris-HCl (50 mM). The solution was incubated for 30 minutes at 37° C. p-Nitrophenol released was spectrophotometrically assayed by UV at 415 nm. The effect of metal ions on enzyme activity is given in Table IV. When the enzyme was treated with 10 mM of EDTA followed by dialysis against water, the sulfatase activity disappeared. Addition of 1 mM of $Ca^{++}$ to the EDTA treated enzyme fully restored the sulfatase activity (FIG. 3).

TABLE IV

| Effects of Metal Ions on Sulfatase Activity | | |
|---|---|---|
| Metal Ion | Rel. Activity (%) | Inhibit. (%) |
| None | 100 | 0 |
| $CoCl_2$ | 34 | 66 |
| $NiCl_2$ | 59 | 41 |
| $ZnCl_2$ | 18 | 82 |
| $BaCl_2$ | 83 | 17 |
| $CuCl_2$ | 56 | 44 |
| $MnCl_2$ | 34 | 66 |
| $FeCl_2$ | 12 | 88 |
| $CaCl_2$ | 213 | — |
| $HgCl_2$ | 0 | 100 |
| $AlCl_3$ | 67 | 33 |
| $FeCl_3$ | 51 | 49 |

(f) Effect of Enzyme Inhibitors

The protocol used in (e) was followed with the exception that 1 mM of an enzyme inhibitor was used instead of a metal ion. The results are given below in Table V.

TABLE V

| Effect of Enzyme Inhibitors on Sulfatase Activity | |
|---|---|
| Inhibitor | % Inhibit. |
| EDTA | 69 |
| 1,10-Phenanthroline | 60 |
| Cysteine | 18 |
| Citrate | 87 |
| p-Chloromercuribenzoic acid | 78 |
| N-Ethylmaleimide | 35 |
| Iodoacetic acid | 96 |
| 2-Mercaptoethanol | 22 |
| Dithiothreitol | 34 |
| Imidazole | 14 |
| Phenylmethanesulfonyl fluoride | 81 |

(g) Effect of Salts

The protocol used in (e) was followed, except that 5 mM of a salt was used instead of 1 mM of a metal ion. The sulfatase activity was strongly inhibited by phosphate but only moderately by sulfate ions. The results are shown in Table VI.

TABLE VI

| Effect of Salts on Sulfatase Activity | |
|---|---|
| Salt | % Inhibit. |
| None | 0 |
| $K_2HPO_4$ | 100 |
| NaCl | 58 |
| KCl | 36 |
| $(NH_4)_2SO_4$ | 44 |
| $K_2SO_4$ | 36 |
| $K_2SO_3$ | 64 |

(h) Substrate Specificity

Four etoposide derivatives were tested as substrate for the sulfatase of the invention. The substrates are: etoposide 4'-sulfate (III), 2",3"-di-O-acetyl-etoposide-4'-sulfate (IV), etoposide 2"-sulfate (V), and etoposide 3"-sulfate (VI). The substrate (50 μl, 1 mg/ml, MeOH:-$H_2O$=1:1, pH 9.0) and the enzyme (50 μl, 0.6 u, 50 mM Tris-HCl, pH 7.5) were mixed and incubated at 37° C. for 30 minutes. The mixture was then analyzed on a silica gel TLC plate using a solvent system consisting of chloroform-methanol (10:1 v/v). The results indicate that, under these test conditions, compounds (III) and (IV) are substrates for the enzyme whereas compounds (V) and (VI) are not. The substrates, compounds (III), (V), and (VI), are known compounds described in Japan Kokai 88/192,793 and our co-pending U.S. patent application U.S. Ser. No. 264,940, filed Oct. 31, 1988; the portions of the disclosure of U.S. Ser. No. 264,940 relating to the preparation of compounds (III), (V), and (VI) are hereby incorporated by reference. Compound (IV) was preapred according to the following procedure: To a solution of 2",3"-di-O-acetyletoposide (170 mg, 0.25 mmol) in pyridine (5 ml) were added dimethylaminopyridine (DMAP, 3 mg, 0.025 mmol) and sulfur trioxide-pyridine complex (199 mg, 1.25 mmol), and the mixture was stirred for 3 days at room temperature. To this mixture were added further DMAP (3 mg, 0.0025 mmol) and sulfur trioxide-pyridine complex (80 mg, 0.5 mmol), and the mixture was stirred at room temperature for 1 day. An additional amount of sulfur trioxide-pyridine complex (199 mg, 1.25 mmol) was added and the mixture was stirred for an additional 2 days. The reaction mixture was concentrated in vacuo below 40° C. to give a crude solid showing two spots on a silica gel TLC plate (Rf 0.9 and 0.2, methylene chloride:methanol=5:1). The crude mixture was subjected to silica gel column chromatography (methylene chloride:methanol=5:1) to provide the starting material (51 mg, Rf 0.9) and the desired sulfate (115 mg, 60%, Rf 0.2). This sulfate (40 mg, 0.054 mmol) was dissolved in a solution of sodium bicarbonate (4.5 mg, 0.054 mmol) in water (4 ml), and the solution was lyophilized to give sodium 2",3"-di-O-acetyletoposide-4'-sulfate (41 mg) as a colorless powder. MP 201° C.-230° C. IRν-max (KBr) $cm^{-1}$ 3350 (br), 1750, 1600.

2",3"-di-O-acetyletoposide used above was prepared according to the procedure provided in our co-pending application U.S. Ser. No. 362,555, filed Jun. 7, 1989; that portion disclosing the preparation of this compound is hereby incorporated by reference.

The characteristics of the arylsulfatase of the present invention render it particularly suitable for clinical use in cancer chemotherapy in which it can be delivered to the vicinity of the tumor where it acts to convert a relatively non-cytotoxic 4'-demethylepipodophyllotoxin glucoside 4'-sulfate into its more cytotoxic parent form. One means of bringing the enzyme close to the tumor is to link the enzyme to an antibody directed to a tumor-associated antigen. This can be accomplished by employing techniques commonly practiced in the art, such as the use of heterobifunctional linkers, examples of which include, but not limited to, N-maleimidobenzoyl succinimide ester, N-succinimidyl-3-(2-pyridyldithio)propionate, and succinimidyl 4-(N-maleimidomethyl)cyclohexane-1-carboxylate. This method is illustrated in Senter, et al., supra.

The ab-enz conjugate and the prodrug may be administered by any conventional route of administration, such as intravenous, intramuscular, intraarterial, oral, intralymphatic, intraperitoneal, and intratumoral. Intravenous is the preferred route. The conjugate and prodrug may be given contemporaneously, but preferably, the conjugate is administered prior to the introduction of the prodrug into the host. Optimal dosages and treatment schedules for a given host will, of course, depend on the prodrug and conjugate chosen and will vary according to the particular composition formulated, the route of administration, and the particular situs, host, and disease being treated. Many factors that modify the action of the therapeutic agents will be taken into account, including age, weight, sex, diet, time of administration, route of administration, rate of excretion, condition of the patient, drug combinations, reaction sensitivities, and severity of the disease.

Although the primary use for the enzyme of the present invention is contemplated as being linked to an antibody and the resultant ab-enz conjugate used in conjunction with a prodrug in the therapy of cancer, other uses for the sulfatase are also envisaged. For example, the sulfatase of the present invention is useful for the degradation of lignosulfonate, a water pollutant generated by the pulp and paper industry.

The following examples are provided to illustrate the present invention and are not to be construed as limiting the scope of the invention in any way.

EXAMPLE 1

Fermentation of Streptomyces sp. T109-3

A loopful of Streptomyces sp. T190-3 grown on agar slant (composed of soluble starch 0.5%, glucose 0.5%, fish meat extract 0.1%, yeast extract 0.1%, NZ-case 0.2%, NaCl 0.2%, $CaCO_3$ 0.1%, and agar 1.6%, pH 7.2) was transferred into liquid medium composed of glucose 1% and yeast extract 1% (pH 7.0) and incubated for 4 days at 27° C. on a rotary shaker set at 200 rpm. A 1 ml aliquot of the culture was inoculated into a 500 ml Erlenmeyer flask containing 100 ml of a medium composed of sorbitol 2%, yeast extract 2%, malt extract 2%, and $CaCO_3$ 0.1%, pH 7.2, and incubated for 5 days at 27° C. on a rotary shaker set at 200 rpm.

EXAMPLE 2

Isolation and Purification of Arylsulfatase

Fermentation broth from 60 flasks was filtered to yield 5.14L of filtrate (stage 1) which was concentrated to 350 ml (stage 2) by ultrafiltration at room temperature using an ultrafiltration module (Asahi Kasei Co.) having a nominal molecular weight cutoff of 6,000. Ammonium sulfate was added to this concentrated protein solution to achieve 80% (w/v) saturation, and the solution was allowed to stand at 4° C. overnight. Protein was collected by centrifugation at 13,000 rpm for 15 minutes at 4° C. The precipitate was then dissolved in 50 mM Tris-HCl, pH 7.5, dialyzed against several changes of the same buffer containing 1 mM $CaCl_2$, and centrifuged at 13,000 rpm for 15 minutes. The supernatant (25 ml, stage 3) was applied to a column (1.5×6 cm) of Sulfate-Cellulofine (Seikagaku Kogyo Co.) which had been equilibrated with 50 mM Tris-HCl buffer, pH 7.5. The column was eluted with 1M Tris-HCl buffer, pH 7.5, and the eluate was collected in 5 ml fractions. Fractions containing enzyme activity were combined (35 ml, stage 4) and applied to a column (1.5×6 cm) of DEAE-Cellulose (Seikagaku Kogyo Co.) which had been equilibrated with 50 mM Tris-HCl buffer, pH 7.5. The column was developed with a linear concentration gradient of Tris-HCl, pH 7.5, from 50 mM to 500 mM. Fractions containing enzyme activity were combined (100 ml, stage 5) and again applied to a column (1.5×4.5 cm) of Sulfate Cellulofine which had been equilibrated with 50 mM Tris-HCl, pH 7.5. The column was eluted with a linear concentration gradient of Tris-HCl, pH 7.5, from 50 mM to 1.5M. Enzyme-containing fractions were combined and concentrated to 10 ml (stage 6) using an ultrafiltration module UHP-43 (Advantec Co.). This preparation showed a single protein band on SDS-PAGE analysis.

The result after each purification step is provided in the chart below:

| Stage | Total Volume (ml) | Total Protein (mg) | Total Sulfatase Activity (U) | Specific Activity (U/mg) | Fold Increase | Recovery (%) |
|---|---|---|---|---|---|---|
| 1. Crude | 5,140 | 3,084 | 111,960 | 36.3 | 1 | 100 |
| 2. UF-Module | 350 | 2,636 | 104,122 | 39.5 | 1.09 | 93 |
| 3. $(NH_4)_2SO_4$ | 25 | 2,112 | 96,000 | 45.5 | 1.25 | 85.7 |
| 4. Sulfate-Cellulofine (1st) | 35 | 25.55 | 85,120 | 3,331.5 | 91.8 | 76.0 |
| 5. DEAE-Cellulose | 100 | 4.0 | 38,120 | 9,600 | 264.5 | 34.3 |
| 6. Sulfate-Cellulofine (2nd) | 10 | 0.945 | 18,750 | 19,841.2 | 546.6 | 16.7 |

We claim:

1. A substantially purified sulfatase isolated from Streptomyces sp. T109-3, said sulfatase being capable of catalyzing the conversion of a 4'-demethylepipodophyllotoxin glucoside 4'-sulfate into a 4'-demethylepipodophyllotoxin glucoside and characterized by having a molecular weight of about 45 kD as determined by SDS-PAGE, an optimal pH of about 9.0 when using p-nitrophenylsulfate as the substrate and an isoelectric point of about 5.6.

2. A substantially purified sulfatase isolated from Streptomyces sp. T109-3, said sulfatase being capable of catalyzing the conversion of etoposide 4'-sulfate into etoposide and characterized by having a molecular weight of about 45 kD as determined by SDS-PAGE, an optimal pH of about 9.0 when using p-nitrophenylsulfate as the substrate and an isoelectric point of about 5.6.

3. A substantially purified sulfatase isolated from Streptomyces. sp. T109-3, said sulfatase being capable of catalyzing the conversion of 2",3"-di-O-acetyl-etoposide 4'-sulfate into 2",3"-di-O-acetyl-etoposide and is characterized by having a molecular weight of about 45 kD as determined by SDS-PAGE, an optimal pH of about 9.0 when using p-nitrophenylsulfate as the substrate and an isoelectric point of about 5.6.

* * * * *